(12) United States Patent
Sweeney (10) Patent No.: US 9,615,863 B2
(45) Date of Patent: Apr. 11, 2017

(54) MULTICHANNEL CANNULA FOR KYPHOPLASTY AND METHOD OF USE

(71) Applicant: Spinal Generations, LLC, Mokena, IL (US)

(72) Inventor: Patrick J. Sweeney, Flossmoor, IL (US)

(73) Assignee: Spinal Generations, LLC, Mokena, IL (US)

( * ) Notice: Subject to any disclaimer, the term of this patent is extended or adjusted under 35 U.S.C. 154(b) by 0 days.

(21) Appl. No.: 14/521,108

(22) Filed: Oct. 22, 2014

(65) Prior Publication Data

US 2016/0113690 A1   Apr. 28, 2016

(51) Int. Cl.
*A61B 17/88*   (2006.01)
*A61B 17/70*   (2006.01)

(52) U.S. Cl.
CPC ...... *A61B 17/7083* (2013.01); *A61B 17/8811* (2013.01); *A61B 17/8855* (2013.01)

(58) Field of Classification Search
CPC ............ A61B 17/8808; A61B 17/8811; A61B 17/8816
See application file for complete search history.

(56) References Cited

U.S. PATENT DOCUMENTS

| | | |
|---|---|---|
| 3,310,051 A | 3/1967 | Schulte |
| 4,099,528 A | 7/1978 | Sorenson et al. |
| 4,399,814 A | 8/1983 | Pratt et al. |
| 4,464,178 A | 8/1984 | Dalton |

(Continued)

FOREIGN PATENT DOCUMENTS

| | | |
|---|---|---|
| EP | 0 858 775 | 8/1998 |
| EP | 1 653 869 A1 | 6/2011 |

(Continued)

OTHER PUBLICATIONS

Cecil, M.L. et al., "Projection of the S2 Pedicle Onto the Posterolateral Surface of the Ilium—A Technique for Lag Screw Fixation of Sacral Fractures or Sacroiliac Joint Dislocations," Spine 1996, vol. 21, pp. 875-878, www.kalindra.com/project.htm, 6 pages.

(Continued)

*Primary Examiner* — Eduardo C Robert
*Assistant Examiner* — Julianna N Harvey
(74) *Attorney, Agent, or Firm* — Foley & Lardner LLP (57) ABSTRACT

A method of using a multichannel cannula to perform kyphoplasty includes inserting a stabilizing wire into a vertebra damaged by a compression fracture and inserting, over the stabilizing wire, a cannula. The cannula includes a first channel having open proximal and distal ends, and is configured to receive the stabilizing wire, and a second channel having an inlet portal and an exit portal that are in fluid communication. The cannula further includes an expandable portion configured to expand away from the cannula from an outer wall of the second channel. The method also includes inflating the expandable portion to create a void in the bone and to restore the height of the vertebra, and then deflating the expandable portion. When the void has been created, bone cement is delivered through the second channel into the void via the exit portal to at least partially fill the void.

13 Claims, 13 Drawing Sheets

(56) References Cited

U.S. PATENT DOCUMENTS

| | | | |
|---|---|---|---|
| 4,653,487 A | 3/1987 | Maale | |
| 4,653,489 A | 3/1987 | Tronzo | |
| 4,760,844 A | 8/1988 | Kyle | |
| 4,772,261 A | 9/1988 | Von Hoff et al. | |
| 4,976,692 A | 12/1990 | Atad | |
| 5,047,030 A | 9/1991 | Draenert | |
| 5,195,962 A | 3/1993 | Martin et al. | |
| 5,203,770 A | 4/1993 | Wigness et al. | |
| 5,250,055 A | 10/1993 | Moore et al. | |
| 5,380,276 A | 1/1995 | Miller et al. | |
| 5,380,319 A | 1/1995 | Saito et al. | |
| 5,425,723 A | 6/1995 | Wang | |
| 5,501,667 A * | 3/1996 | Verduin, Jr. | A61M 25/1002 604/101.01 |
| 5,618,286 A | 4/1997 | Brinker | |
| 5,681,289 A | 10/1997 | Wilcox et al. | |
| 5,702,372 A | 12/1997 | Nelson | |
| 5,749,883 A | 5/1998 | Halpern | |
| 5,800,407 A | 9/1998 | Eldor | |
| 5,833,652 A | 11/1998 | Preissman et al. | |
| 5,871,484 A | 2/1999 | Spievack et al. | |
| 5,951,160 A | 9/1999 | Ronk | |
| 6,004,310 A | 12/1999 | Bardsley et al. | |
| 6,019,761 A | 2/2000 | Gustilo | |
| 6,048,343 A | 4/2000 | Mathis et al. | |
| 6,077,265 A | 6/2000 | Werding et al. | |
| 6,146,373 A | 11/2000 | Cragg et al. | |
| 6,179,809 B1 | 1/2001 | Khairkhahan et al. | |
| 6,210,376 B1 | 4/2001 | Grayson | |
| 6,214,012 B1 | 4/2001 | Karpman et al. | |
| 6,220,888 B1 | 4/2001 | Correa | |
| 6,228,088 B1 | 5/2001 | Miller et al. | |
| 6,364,856 B1 | 4/2002 | Ding et al. | |
| 6,387,098 B1 | 5/2002 | Cole et al. | |
| 6,440,141 B1 | 8/2002 | Philippon | |
| 6,461,327 B1 | 10/2002 | Addis et al. | |
| 6,533,782 B2 | 3/2003 | Howell et al. | |
| 6,629,947 B1 | 10/2003 | Sahatjian et al. | |
| 6,663,596 B2 | 12/2003 | Griego et al. | |
| 6,679,890 B2 | 1/2004 | Margulies et al. | |
| 6,780,167 B2 | 8/2004 | Leone | |
| 6,921,380 B1 | 7/2005 | Epstein et al. | |
| 7,527,611 B2 | 5/2009 | Sweeney | |
| 7,575,572 B2 | 8/2009 | Sweeney | |
| 7,608,062 B2 | 10/2009 | Sweeney | |
| 7,632,294 B2 | 12/2009 | Milbodker et al. | |
| 7,678,098 B2 | 3/2010 | Bertolero et al. | |
| 7,717,956 B2 | 5/2010 | Lang | |
| 7,901,407 B2 | 3/2011 | Olson et al. | |
| 8,057,090 B1 | 11/2011 | Saha et al. | |
| 8,062,270 B2 | 11/2011 | Sweeney | |
| 8,241,245 B2 | 8/2012 | Markel et al. | |
| 8,303,598 B2 | 11/2012 | Frankel et al. | |
| 8,597,301 B2 | 12/2013 | Mitchell | |
| 8,617,585 B2 | 12/2013 | Boden et al. | |
| 8,684,965 B2 | 4/2014 | Rabiner et al. | |
| 8,808,337 B2 | 8/2014 | Sweeney | |
| 8,870,836 B2 | 10/2014 | Sweeney | |
| 2001/0021852 A1 | 9/2001 | Chappius | |
| 2002/0138146 A1 | 9/2002 | Jackson | |
| 2003/0045885 A1 | 3/2003 | Margulies et al. | |
| 2003/0050644 A1* | 3/2003 | Boucher | A61B 17/3472 606/90 |
| 2003/0083662 A1 | 5/2003 | Middleton | |
| 2003/0139751 A1 | 7/2003 | Evans et al. | |
| 2003/0212426 A1 | 11/2003 | Olson et al. | |
| 2004/0006341 A1 | 1/2004 | Shaolian et al. | |
| 2004/0225292 A1 | 11/2004 | Sasso et al. | |
| 2005/0015059 A1 | 1/2005 | Sweeney | |
| 2005/0015060 A1 | 1/2005 | Sweeney | |
| 2005/0059972 A1 | 3/2005 | Biscup | |
| 2005/0090852 A1* | 4/2005 | Layne | A61B 17/3417 606/190 |
| 2006/0111767 A1 | 5/2006 | Olson et al. | |
| 2006/0122625 A1* | 6/2006 | Truckai | A61B 17/8822 606/94 |
| 2006/0253081 A1 | 11/2006 | Paulos et al. | |
| 2007/0083265 A1 | 4/2007 | Malone | |
| 2007/0154460 A1 | 7/2007 | Kraft et al. | |
| 2007/0225219 A1 | 9/2007 | Boden et al. | |
| 2008/0039846 A1 | 2/2008 | Lee et al. | |
| 2008/0039855 A1 | 2/2008 | Lambert | |
| 2008/0058828 A1* | 3/2008 | Reiley | A61B 10/025 606/94 |
| 2009/0088604 A1 | 4/2009 | Lowry et al. | |
| 2009/0164016 A1 | 6/2009 | Georgy et al. | |
| 2009/0204158 A1 | 8/2009 | Sweeney | |
| 2009/0301643 A1* | 12/2009 | Tilson | A61B 17/8816 156/155 |
| 2010/0131014 A1 | 5/2010 | Peyrot et al. | |
| 2010/0262069 A1 | 10/2010 | Rabiner et al. | |
| 2010/0262089 A1 | 10/2010 | Sweeney | |
| 2011/0224494 A1 | 9/2011 | Piskun et al. | |
| 2011/0224741 A1 | 9/2011 | Forrest | |
| 2012/0029432 A1 | 2/2012 | Sweeney | |
| 2012/0041395 A1 | 2/2012 | Sweeney | |
| 2012/0109102 A1 | 5/2012 | Vandewalle | |
| 2012/0221009 A1 | 8/2012 | Tada et al. | |
| 2012/0330320 A1 | 12/2012 | Takizawa et al. | |
| 2013/0158471 A1 | 6/2013 | Neel et al. | |
| 2014/0128877 A1 | 5/2014 | O'Halloran et al. | |
| 2014/0142550 A1 | 5/2014 | Sweeney | |
| 2014/0142584 A1 | 5/2014 | Sweeney | |
| 2014/0276596 A1 | 9/2014 | Vandewalle | |

FOREIGN PATENT DOCUMENTS

| | | |
|---|---|---|
| WO | WO-02/098307 A1 | 12/2002 |
| WO | WO-2005/009258 A1 | 2/2005 |
| WO | WO-2008/121609 | 10/2008 |
| WO | WO-2010/019788 | 2/2010 |

OTHER PUBLICATIONS

Communication received in European Patent Application No. 11250603.5, dated Feb. 20, 2015, 5 pages.

European Search Report for European Patent Application No. 11250603.5-2310, dated Sep. 29, 2011, 6 pages.

Instratek Inc., "Titanium Cannulated Bone Screws Minimize Surgery Time by Eliminating Complicated Procedure Steps," www.instratek.com/bone_screw/, 5 pages.

International Search Report and Written Opinion for International Application No. PCT/US2014/035542, dated Sep. 22, 2014, 14 pages.

International Search Report and Written Opinion for PCT Application No. PCT/US2013/070384, mail date Mar. 20, 2014, 13 pages.

International Search Report and Written Opinion for PCT application No. PCT/US2014/063906, dated Feb. 9, 2015, 13 pages.

International Search Report and Written Opinion for PCT Application PCT/US2013/052853, dated Jan. 14, 2014, 15 pages.

International Search Report and Written Opinion for PCT Application No. PCT/US2015/014216, dated Apr. 22, 2015, 14 pages.

Press release from Spine Center Atlanta, "New Screw Debut Firsttime Use for New Spinal Surgery Device," 2002, Orthopaedic & Spine Surgery of Atlanta, LLC. www.SpineCneterAtlanta.com, 2 pages.

Sato, T. et al., "Calcium Phosphate Augmentation of Screw Fixation in Femoral Neck Fracture," 47th Annual Meeting, Orthopaedic Research Society, Feb. 25-28, 2001, San Francisco, CA, 1 page.

SunMedica—Orthopaedic Surgery Products, "orthoPLUG® Hard Bone Design," Redding, CA 96002; www.xunmedica.com, 1 page.

International Search Report and Written Opinion for PCT Application No. PCT/US2015/055783, mail date Jan. 22, 2016, 16 pages.

\* cited by examiner

MULTICHANNEL CANNULA FOR KYPHOPLASTY AND METHOD OF USE

BACKGROUND

The present invention relates generally to the field of devices and methods for delivering substances to bone. More particularly, the present invention concerns devices and methods for performing a kyphoplasty procedure to treat conditions of the spine.

Kyphoplasty is a procedure used to treat painful compression fractures in the spine. When the compression fracture occurs, part of a spine bone collapses. Compression fractures are often caused by osteoporosis resulting in softening and weakening of the vertebrae. Small fractures in the bone can eventually cause the vertebra to collapse, thereby creating the spinal compression fracture. Compression fractures can occur suddenly, and severe pain usually results from the fracture. Most often, compression fractures occur in the softer bone of the front of the vertebra. When the front part of the bone collapses, a wedge-shaped vertebra may result. Many compression fractures in the front of the vertebrae may eventually cause kyphosis, which is a hump-like curvature of the spine (sometimes referred to as a dowager's hump). Other symptoms of compression fractures include tenderness at the spine, back pain that gets worse with walking, but usually not felt while resting, and loss of height.

Conventional methods of performing a kyphoplasty procedure make use of balloon like device to create space in the bone to compensate for the deformity caused by the compression fracture, and then filling the void with bone cement. More specifically, one method includes advancing a biopsy needle into the pedicle of the vertebra, under fluoroscopic guidance, and inserting a cannula over the needle. Once the cannula is positioned, the needle is removed from the pedicle. An inflatable catheter or balloon tamp is then inserted through the cannula and into the collapsed portion of the vertebra. The balloon is then slowly inflated to create a void in the bone. Once the void is created, the inflatable catheter or balloon tamp is removed in preparation to receive the bone cement. A bone cement delivery device, such as a delivery needle is then inserted into the cannula and the bone cement is delivered to the void created by the inflated balloon. When the bone cement has cured, the cannula and the delivery device is removed, to complete the procedure.

The conventional methods, such as that described above, involve multiple steps that require the introduction and removal of various tools throughout the process. Not only is this process cumbersome, but also time consuming. If the procedure is necessary for multiple vertebrae, the time and the complexity of the process multiplies. Also, if additional space needs to be created in the vertebra before the procedure is complete, the cement delivery device must be removed and replaced by the inflatable device, which is re-inflated, and then the delivery device re-introduced to deliver the remainder of the cement.

SUMMARY

The embodiments described herein provide a multichannel cannula configured to efficiently perform both bone void creation and bone cement delivery in a kyphoplasty procedure. The device and method embodiments described herein may also be used for bone void creation and material delivery in other bones of the body, including, but not limited to treatment for fractures in the heel bone or the tibial plateau.

One embodiment of the invention relates to a method of using a multichannel cannula to perform kyphoplasty including inserting a stabilizing wire into a vertebra that is damaged by a compression fracture and inserting, over the stabilizing wire, a multichannel cannula into the vertebra. The multichannel cannula includes a first channel having an open proximal end and an open distal end, wherein the first channel is configured to receive the stabilizing wire, a second channel having an inlet portal and an exit portal, wherein the inlet portal and the exit portal are in fluid communication, and an expandable portion configured to expand away from the multichannel cannula from an outer wall of the second channel. The method further includes inflating the expandable portion to create a void in the bone and to restore the height of the vertebra that was compromised by the compression fracture. Once the void has been created, the expandable portion is deflated. The method further includes delivering bone cement through the second channel into the void via the exit portal to at least partially fill the void and retain the restored height of the vertebra.

Another embodiment of the invention relates to a multichannel cannula for performing kyphoplasty, the cannula including a first channel having an open proximal end and an open distal end, wherein the first channel is configured to receive a stabilizing wire, and a second channel having an inlet portal and an exit portal, wherein the inlet portal and the exit portal are in fluid communication to deliver bone cement to a void in a bone. The cannula further includes an expandable portion configured to expand away from the multichannel cannula from an outer wall of the second channel to create the void in the bone.

Yet another embodiment of the invention relates to a method of using a multichannel cannula to deliver a material to a void in a bone, including inserting a stabilizing wire into a bone and inserting, over the stabilizing wire, a multichannel cannula into the bone. The multichannel cannula includes a first channel having an open proximal end and an open distal end, wherein the first channel is configured to receive the stabilizing wire, and a second channel having an inlet portal and an exit portal, wherein the inlet portal and the exit portal are in fluid communication. The cannula further includes an expandable portion configured to expand away from the multichannel cannula from an outer wall of the second channel. The method also includes the steps of inflating the expandable portion to create a void in the bone, and then deflating the expandable portion. When the void is created, the method includes delivering a material through the second channel into the void via the exit portal to at least partially fill the void.

Alternative exemplary embodiments relate to other features and combinations of features as may be generally recited in the claims.

BRIEF DESCRIPTION OF THE FIGURES

The disclosure will become more fully understood from the following detailed description, taken in conjunction with the accompanying figures, wherein like reference numerals refer to like elements, in which.

DETAILED DESCRIPTION

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting. It should also be understood that while the description herein refers to kyphoplasty of the vertebra having a compression fracture, the devices and methods according to the disclosed embodiments may also be used to treat fractures and other damage in other bones of the body. Some alternative uses of the disclosed embodiments may be, for example, treatment of the heel bone or the tibial plateau.

According to exemplary embodiments as disclosed herein, a multichannel cannula is provided to be used in a kyphoplasty procedure to create the void in the bone by way of one or more balloons and to deliver the bone cement to the created void, thereby making use of a single device which remains inserted into the vertebra throughout the kyphoplasty procedure. The multichannel cannula configured for a kyphoplasty procedure may be similar to the cannulas as described in U.S. patent application Ser. No. 13/270,072, titled "Method and Device for Delivering Medicine to Bone," filed Oct. 10, 2011, and U.S. patent application Ser. No. 14/081,784, titled "Method and Device for Delivering Medicine to Bone," filed Nov. 15, 2013, both of which are hereby incorporated by reference herein in their entireties.

Figure 1:
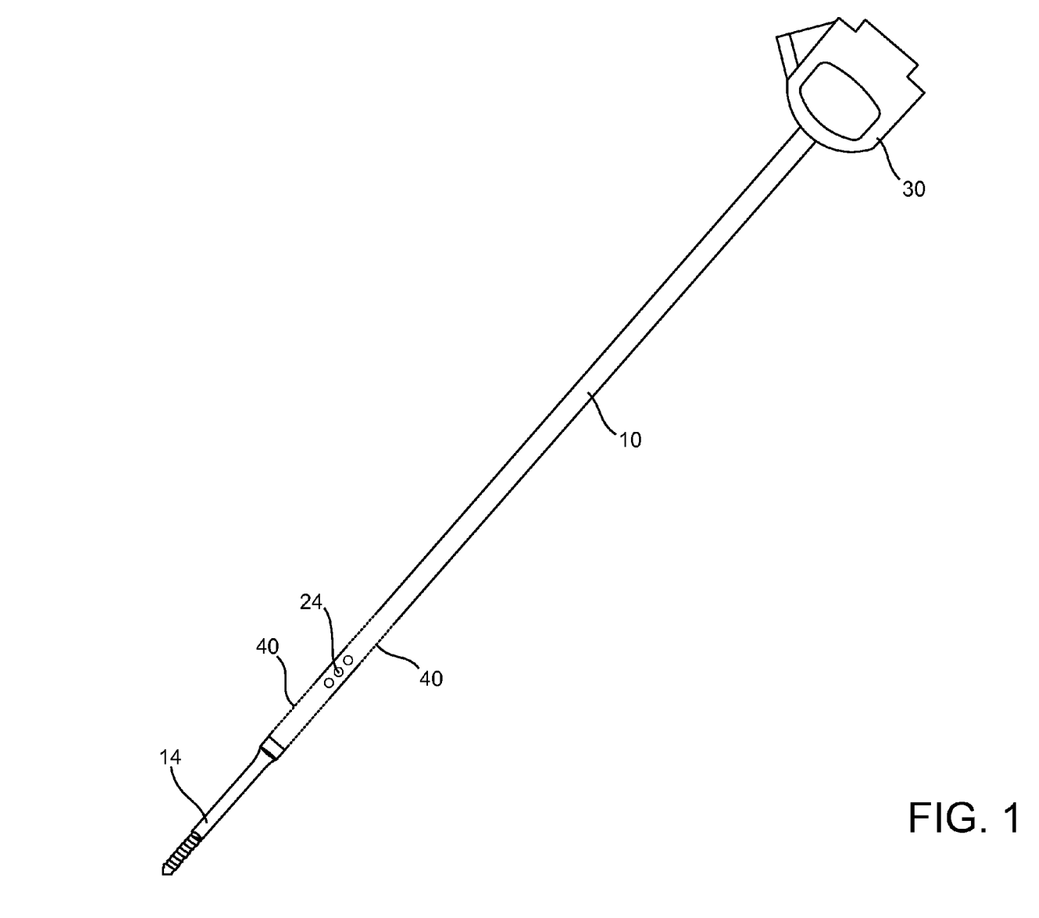
FIG. 1 illustrates a perspective view of a multichannel cannula according to an exemplary embodiment.
Figure 2:
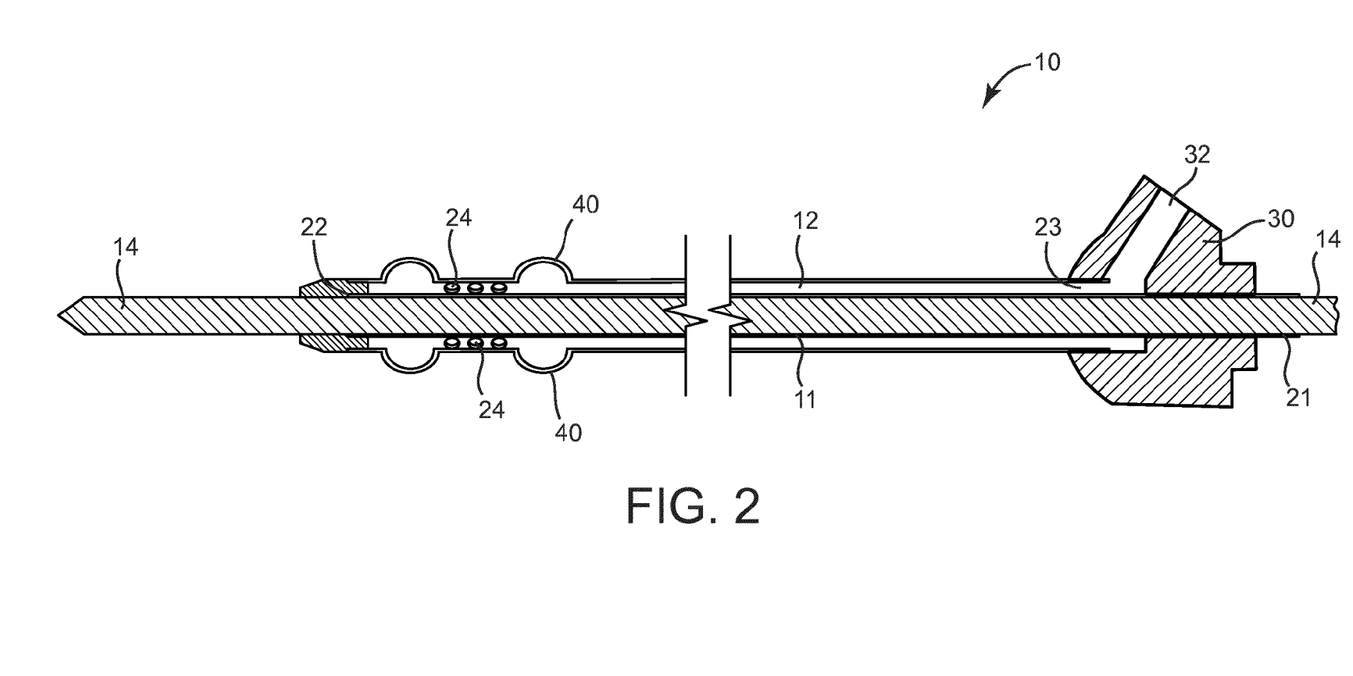
FIG. 2 illustrates a cross-sectional view of the multichannel cannula of FIG. 1.

FIGS. 1 and 2 depict a multichannel cannula 10, according to an exemplary embodiment, having at least two coaxial channels 11, 12. A first channel 11 of the multichannel cannula 10 is configured to receive a stabilizing wire 14 therethrough. The second channel 12 of the multichannel cannula 10 is configured to be used for delivering a surgical substance to the interior of a bone, such as vertebra 100 (see FIG. 6). The substance delivered using the multichannel cannulas described herein may be any type of substance a user desires to deliver to the interior of a bone, including growth factors or medication such as bone cement, bone void fillers, calcium phosphate paste, an antibiotic, pain medication, or a chemotherapeutic agent. During a kyphoplasty procedure, in particular, the substance is a bone cement and/or a bone void filler.

The cannulas described herein can be made of any material suitable for placement into a bone without harmful effects on the patient. In one embodiment, the cannula is made of stainless steel or other type of metal. In another embodiment, the cannula is made of a rigid plastic, such as polyethylketone, that cannot be easily bent or manipulated into alternative configurations. A rigid cannula may be advantageous to provide stability when introducing the cannula into an aperture 106 in a bone 100 (see FIG. 4). Furthermore, a rigid cannula provides stability for various procedures that a more flexible cannula may not provide. For example, if a surgeon desires to use a plunger or other device to push a substance from the cannula and into the bone, a rigid cannula may be more desirable. As another example, a rigid cannula is able to withstand more significant forces than a flexible cannula (e.g., forces applied to the cannula by a delivery device or a suction device, and the forces resulting from movement of substances through the channels and through any open portals in the cannula).

The multichannel cannula 10 depicted in FIGS. 1 and 2 includes a first channel 11 having an open proximal end 21 and an open distal end 22. The open proximal end 21 and open distal end 21 allow the first channel 11 to be positioned over a stabilizing wire 14. In one embodiment, the first channel 11 is substantially cylindrical and has a diameter slightly larger than the diameter of the stabilizing wire 14. The side wall of the cylindrical first channel 11 (as distinguished from the open ends of the first channel) may be continuous, meaning there are no open portals or other openings along the side wall of the first channel 11. In a preferred embodiment, fluids cannot penetrate the side wall of the first channel 11.

The multichannel cannula 10 depicted in FIGS. 1 and 2 further includes a second channel 12. The second channel 12 includes an inlet portal 23 and an exit portal (e.g., side exit ports 24). In an exemplary embodiment, the second channel 12 surrounds the outer wall of the first channel 11. Preferably, the first channel 11 and the second channel 12 are coaxial. In other embodiments, however, the two channels can be formed in a non-coaxial fashion, may be positioned side-by-side within the cannula body, or the cannula may include more than two channels, such that a plurality of channels surround the first channel 11.

In the methods described herein, the inlet portal 23 of the second channel 12 serves as an inlet for the surgical substance, such as bone cement, to be delivered to the interior of a bone 100. In these embodiments, the exit portal 24 of the second channel 12 serves as an outlet for the substance. The inlet portal 23 and exit portal 24 of the second channel are thus in fluid communication to allow substances or materials to be delivered to the interior of a bone 100 through exit portal 24. In the embodiments shown, the exit portal includes a plurality of side exit ports 24. The cannulas shown have three exit ports 24, but any number may be used to serve as the exit portal and deliver the material to the bone.

As shown in FIGS. 1 and 2, multichannel cannula 10 may also include a cap 30. The cap 30 has a housing portion with a channel for coupling to a portion of the proximal end of cannula 10. The channel of the cap 30 may extend from first end through a second end of the housing portion for receiving the stabilizing wire 14 therethrough. In a preferred embodiment, the cap 30 is affixed to the multichannel cannula 10, such as during production of the cannula 10. In an alternative embodiment, the cap 30 may be removable. The cap 30 may be positioned at the site of the aperture in the bone, such as aperture 106, (not shown) in order to serve as a plug. In this way, cap 30 can plug the aperture 106 and may prevent irrigation or other substance being delivered to the site from coming back up through the aperture 106 in the bone. In another embodiment, a separate temporary plug or seal may be added to the cannula to plug the aperture 106 in the bone. In the embodiment shown, cap 30 also has a delivery portal 32. The delivery portal 32 is coupled to an inlet portal 23 of the second channel 12 such that a substance can flow from the delivery portal 32, through the inlet portal 23, and into the second channel 12.

In some exemplary embodiments, the multichannel cannula may include a plunger to assist with delivery of the bone cement through an exit portal. The plunger is preferably configured to pass through the multichannel cannula in the second channel 12 after a substance has been introduced into the channel 12 through the inlet portal 23. The cap 30 and the plunger may be configured to engage such that a distal portion of the plunger is received in and engages with the channel of the cap 30. The plunger fits around the first channel 11 and capable of being moved within the second channel 12 of the cannula.

Various delivery systems can be coupled to the delivery portal 32 to assist in delivering substances to the second channel 12 of multichannel cannula 10, and ultimately to the bone, such as vertebra 100. The type of delivery system selected by a user may depend on the type of substance to be delivered to the bone. In the embodiments shown in the figures, the delivery system is a syringe coupled with the delivery portal 32 of the cap 30 to provide substance, such as the bone cement, through the cannula to the target portion of the bone.

Once a substance has been delivered to second channel 12 of the multichannel cannula 10 through the inlet portal 23, the substance exits second channel 12 via a side exit port 24 located on an outer wall of the second channel 12. In this embodiment, the distal end of second channel 12 is closed, preventing the substance from exiting the distal end of the second channel 12. However, in an alternative embodiment, the distal end of the second channel 12 may be open to create an exit portal such that the substance can exit the second channel 12 through both the side exit port 24 and the open distal end, or solely through the distal end. During use of multichannel cannula 10, a user may align the side exit port 24 with the area of the bone to be treated with the substance.

In the embodiments shown, the second channel 12 includes one or more expandable portions 40. The expandable portions 40 may be balloons configured to expand between the outside of the cannula 10 and the bone. In a kyphoplasty procedure, the expandable portions 40 are configured to create a void 110 at or near the compression fracture to restore the original height of the vertebra, and in which the bone cement can be delivered. The expandable portions 40 may further provide stabilization to the cannula 10 inserted in the bone and/or may provide a mechanism to isolate certain areas of the bone for delivery of the substance via the cannula 10. A cannula 10 for use during kyphoplasty can have any number of expandable portions. In the embodiment shown in FIGS. 1-2 and 4-7, cannula 10 has two expandable portions 40, one on each side of the set of side exit ports 24. Other embodiments may include any number of expandable portions 40, including a single balloon or a plurality of balloons. Furthermore, expandable portion 40 may be located at positions other than those shown in the figures, such as at the distal end, at a more proximal position from the side exit ports 24, or anywhere along the length of the cannula shaft. One example of an alternative arrangement of the expandable portion and side exit port 24 is shown in FIGS. 9-12, and described below.

Figure 3:
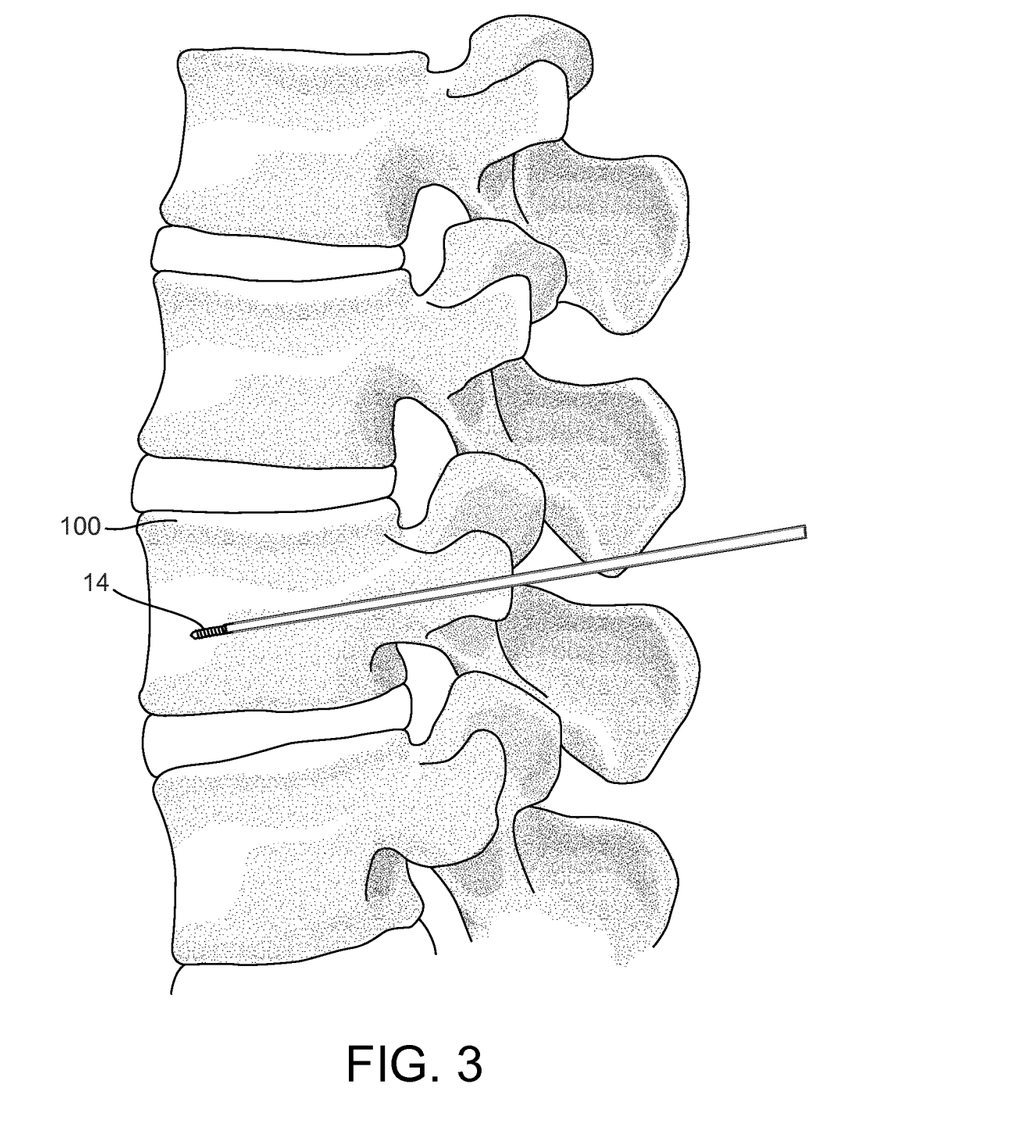
FIG. 3 illustrates inserting a stabilizing wire into a bone for a kyphoplasty procedure.
Figure 4:
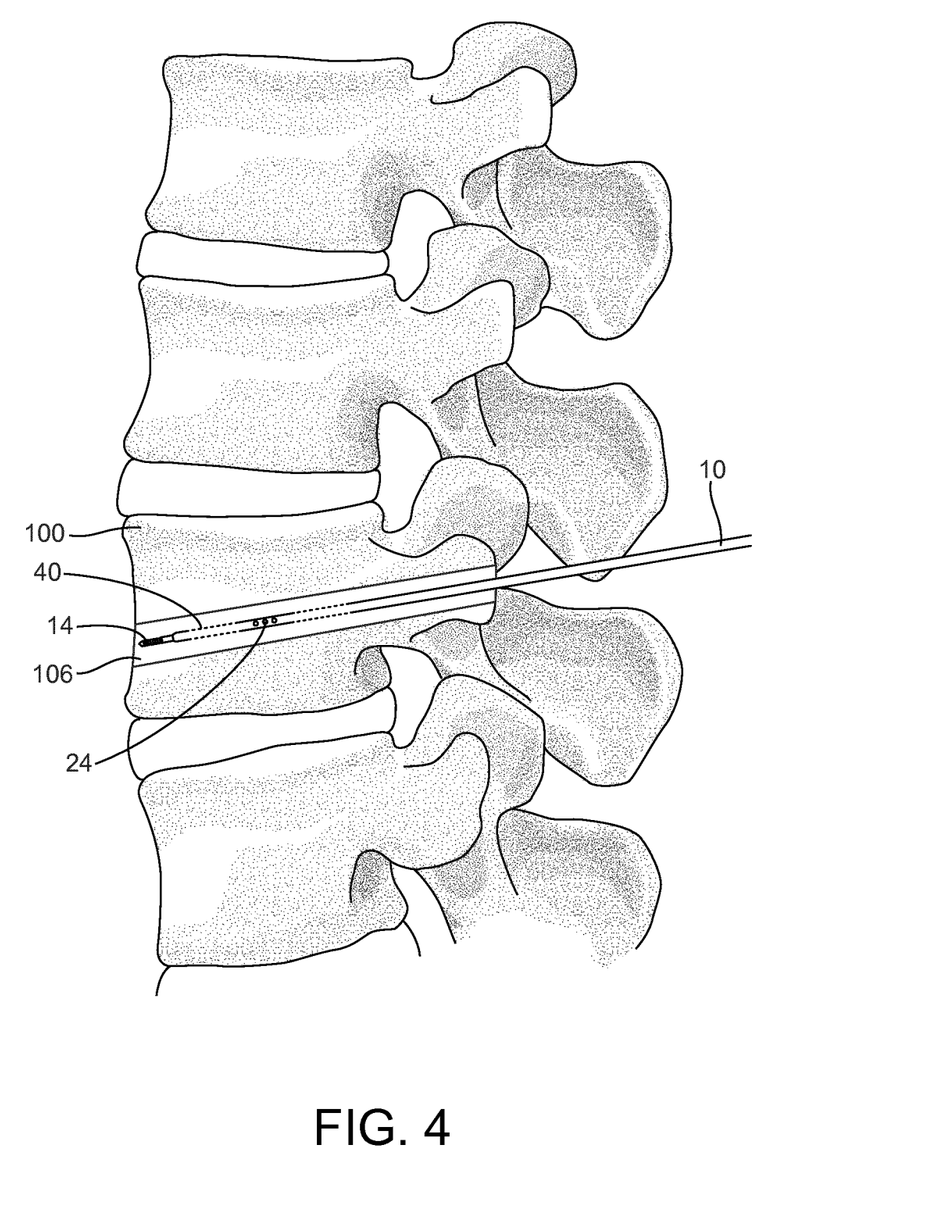
FIG. 4 illustrates positioning a multichannel cannula according to a first embodiment over the stabilizing wire into the bone.
Figure 6:
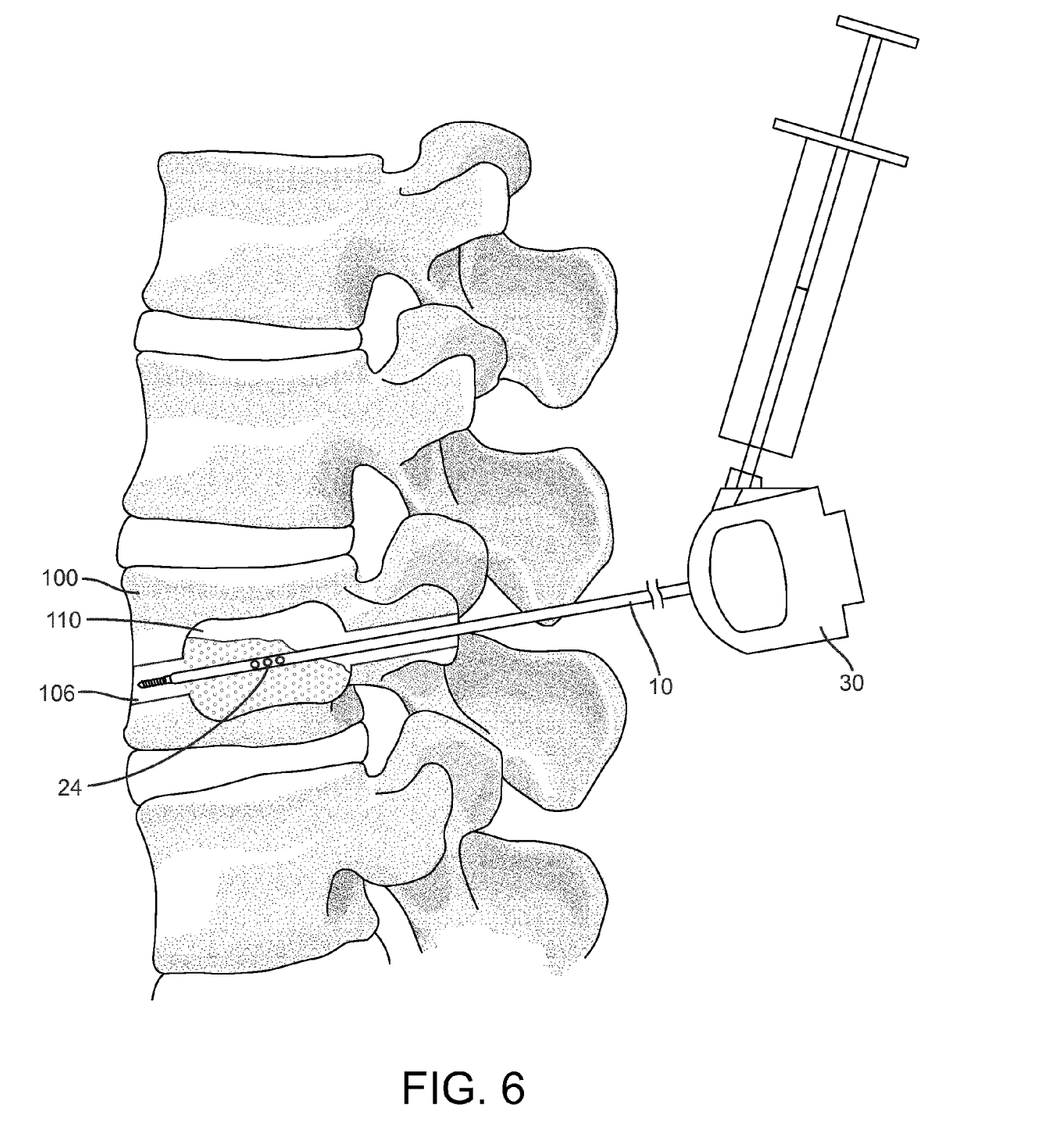
FIG. 6 illustrates delivery of a material to the void in the bone created during the step of FIG. 5.
Figure 7:
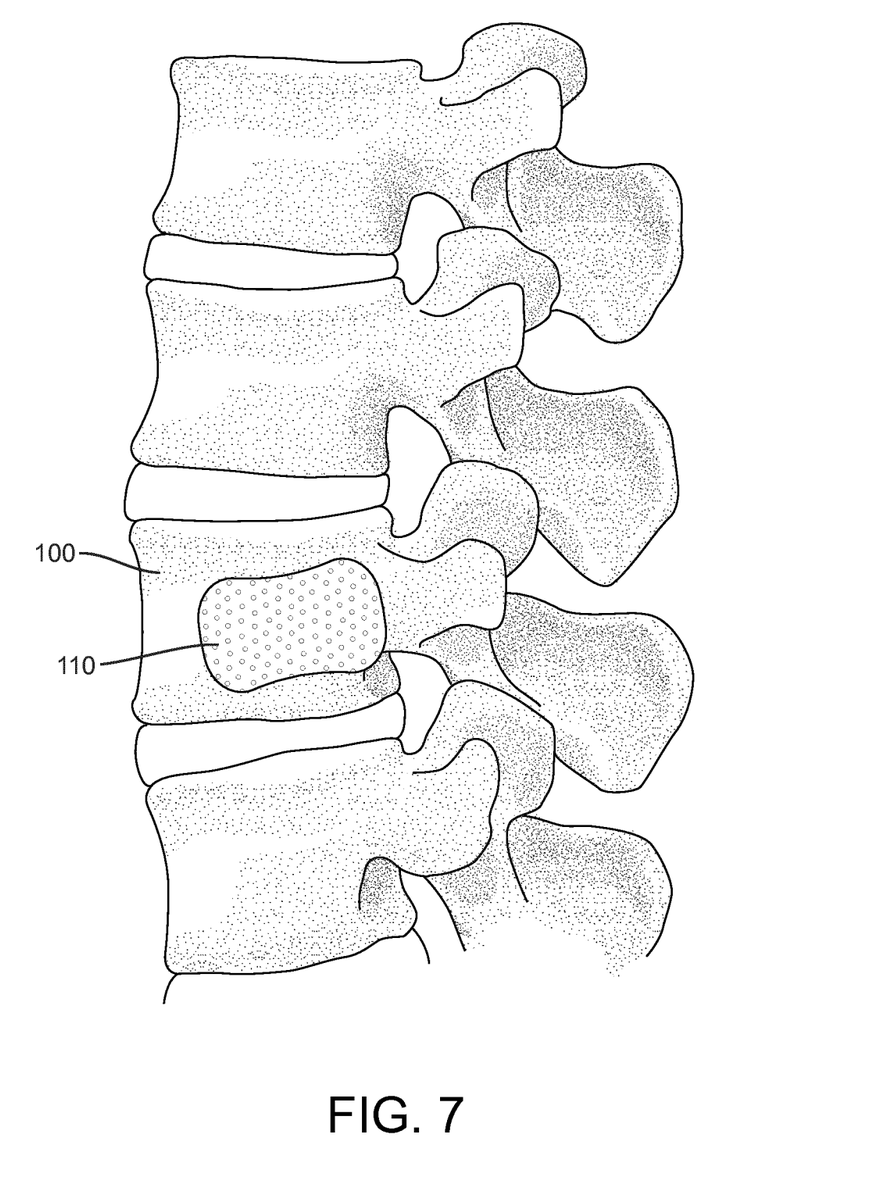
FIG. 7 illustrates the material, such as bone cement, filling the void in the bone.
Figure 8:
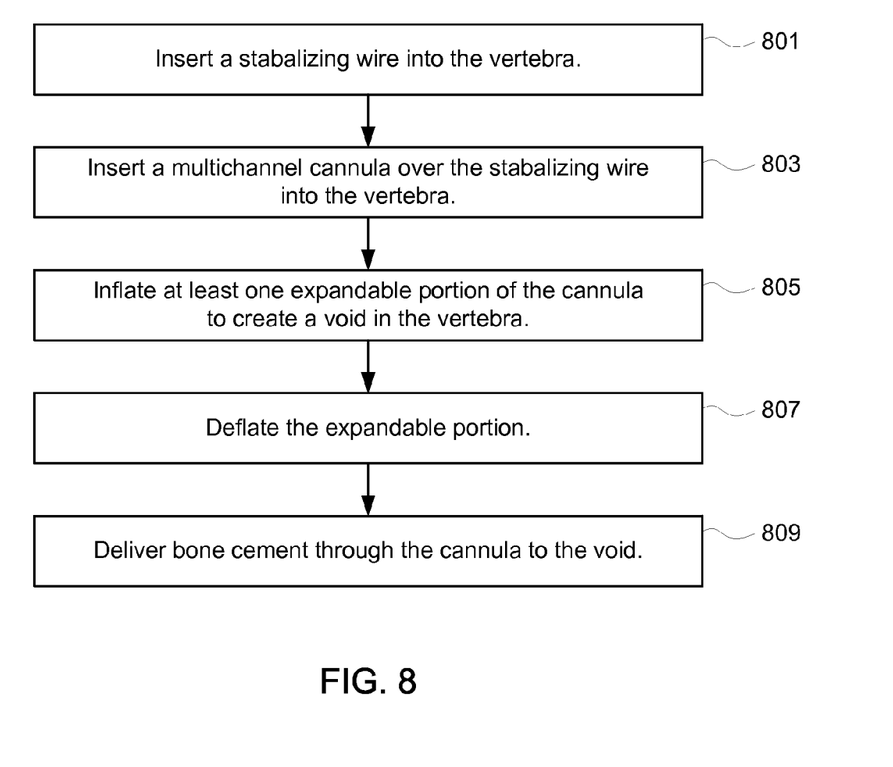
FIG. 8 is a flow chart illustrating the steps of the kyphoplasty method performed in FIGS. 4-7.
Figure 9:
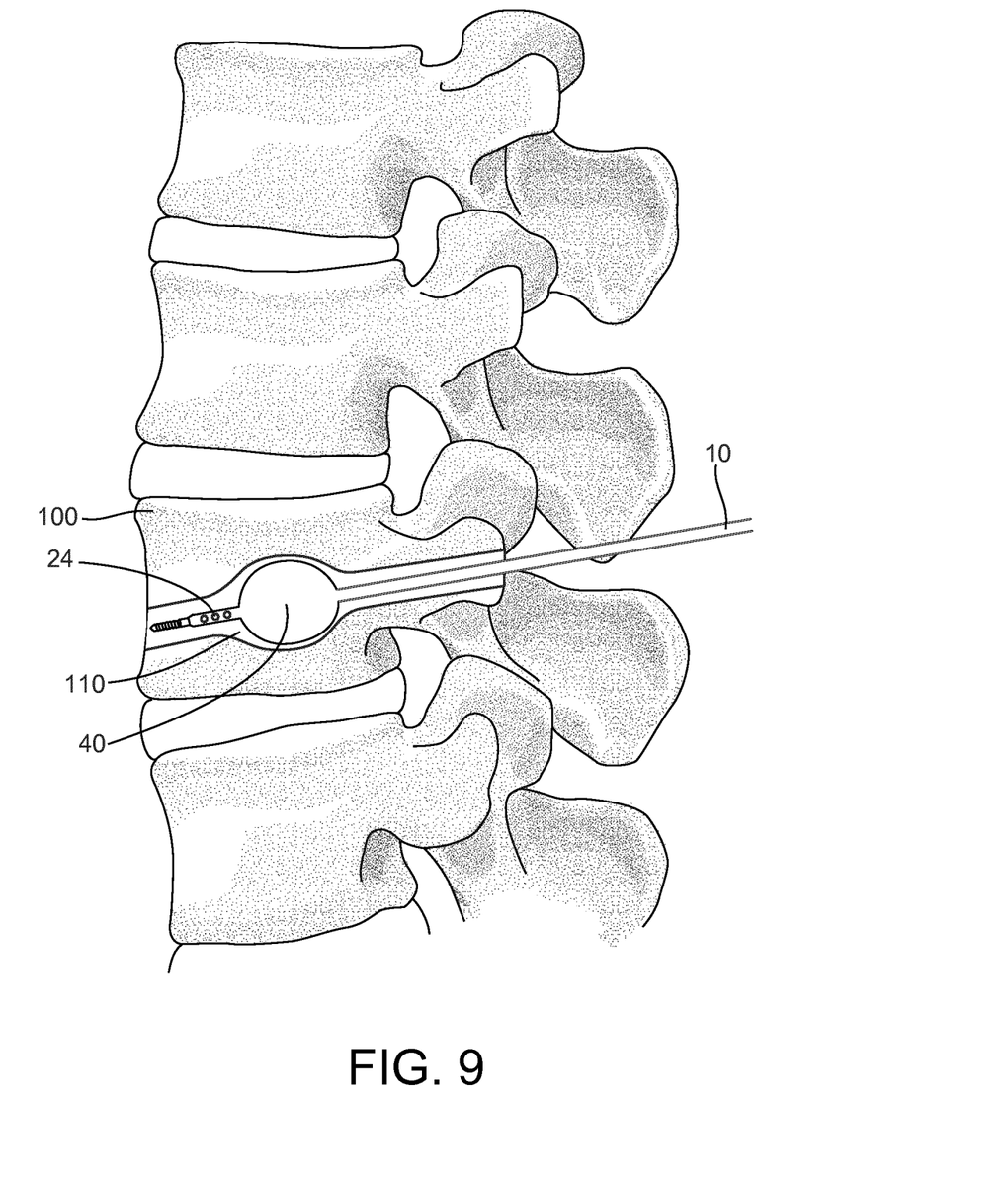
FIG. 9 illustrates inflation of an expandable portion of a multichannel cannula according to a second embodiment to create a void in the bone.

A method for performing a kyphoplasty procedure using multichannel cannula 10, according to an exemplary embodiment, is depicted in FIGS. 3-7 and described in the flowchart of FIG. 8. Step 801 of a kyphoplasty procedure according to an exemplary embodiment is depicted in FIG. 3. A stabilizing wire 14 is inserted or drilled into the pedicle of vertebra 100. Placement of the stabilizing wire 14 is preferably performed under fluoroscopic guidance to accurately reach the target portion of the vertebra, which may be the location of the compression fracture. Then, using a drill, a aperture 106 may be drilled around stabilizing wire 14. Drilled aperture 106 may provide additional space for insertion of cannula 10, a larger diameter cannula, or a catheter into the bone, or provides space for expansion. An aperture 106 provided or created by other means would also be useful to accommodate the cannula or provide the other benefits of aperture 106. In FIG. 4, according to step 803, cannula 10 is threaded over the stabilizing wire 14 into aperture 106 and to the target location in the vertebra 100.

Figure 5:
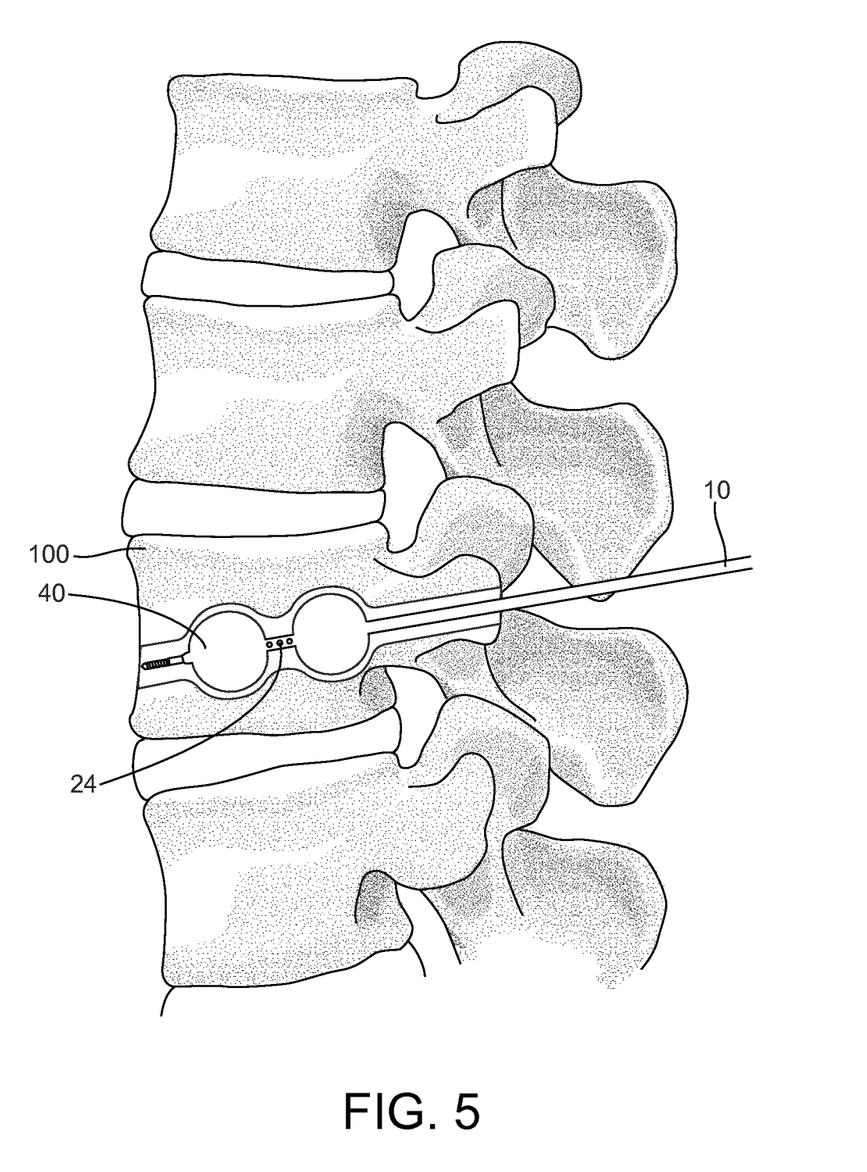
FIG. 5 illustrates inflation of the expandable portions of the multichannel cannula to create a void in the bone.

FIG. 5 depicts the void creating step 805 during kyphoplasty in the vertebra 100. As shown, after positioning the cannula 10 into the bone, the expandable portions 40 of cannula 10 are inflated so as to create void 110 and restore the height of the vertebra. Once the void 110 is created in the bone, the expandable portions are deflated (step 807) as shown in FIG. 6, and the void is filled with a bone cement (step 809), such as methyl methacrylate. If necessary, the expandable portions 40 may be reinflated, either before or after the introduction of the bone cement, to form larger void. Also, it may be necessary to reposition the expandable portion to create a new portion of the void 110 or a new void altogether.

As shown in FIG. 7, when the void 110 has been filled with a desired amount of bone cement, the stabilizing wire 14 and cannula 10 are removed from the bone 100, and the cement cures in the void. In this way, the hardened cement provides support to maintain the height of the vertebra and lessen or eliminate the deformation caused by the compression fracture.

Figure 10:
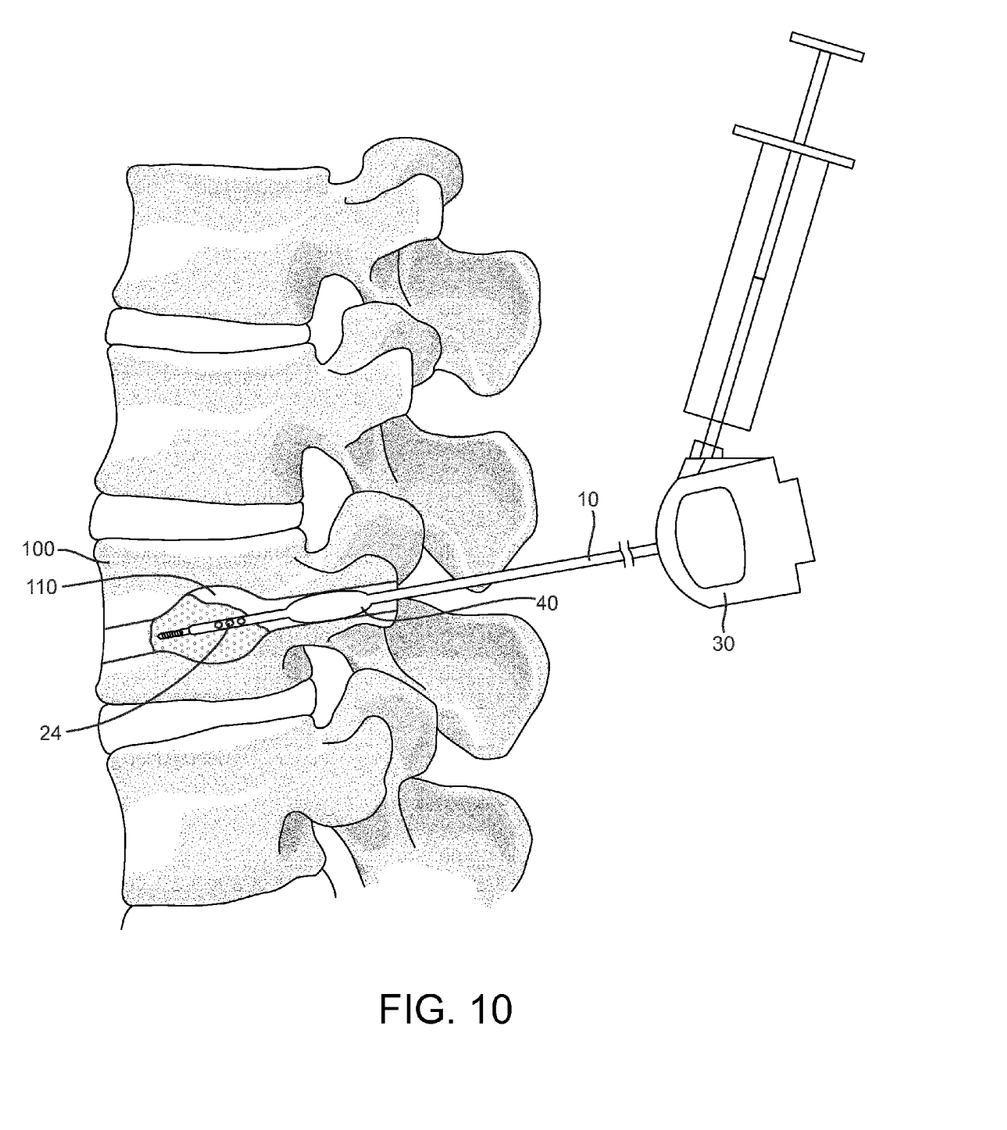
FIG. 10 illustrates delivery of a material to the void in the bone created during the step shown in FIG. 9.
Figure 11:
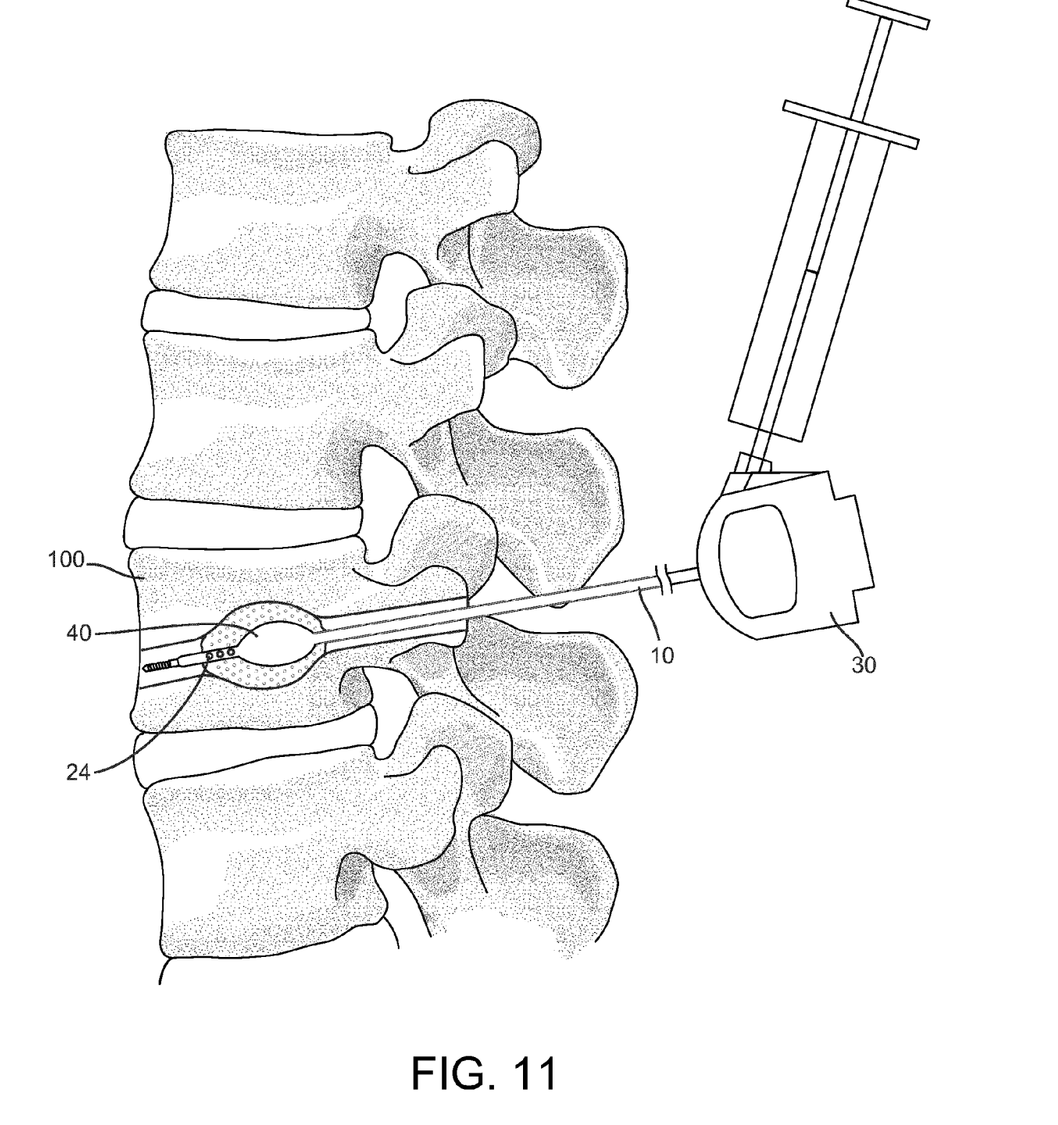
FIG. 11 illustrates inflation of the expandable portion to create a second void within the material delivered in the step shown in FIG. 10.
Figure 12:
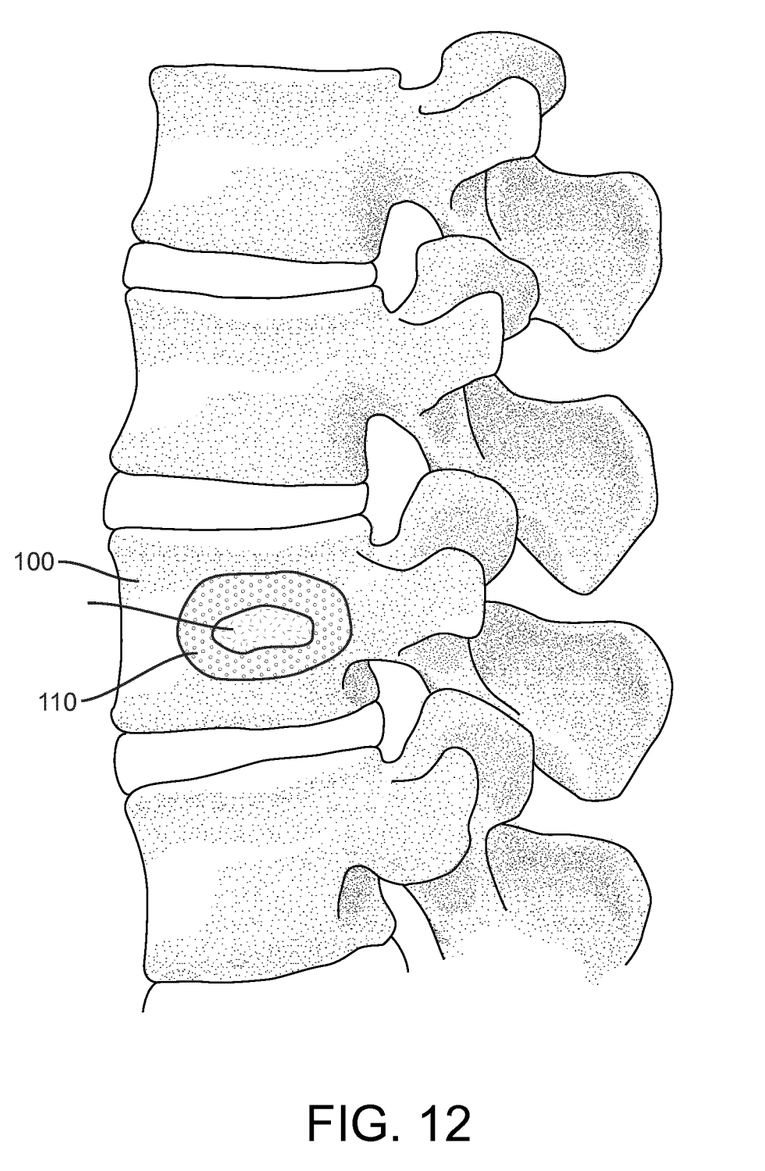
FIG. 12 illustrates a first portion of a material and a second portion of a material filling the void in the bone.
Figure 13:
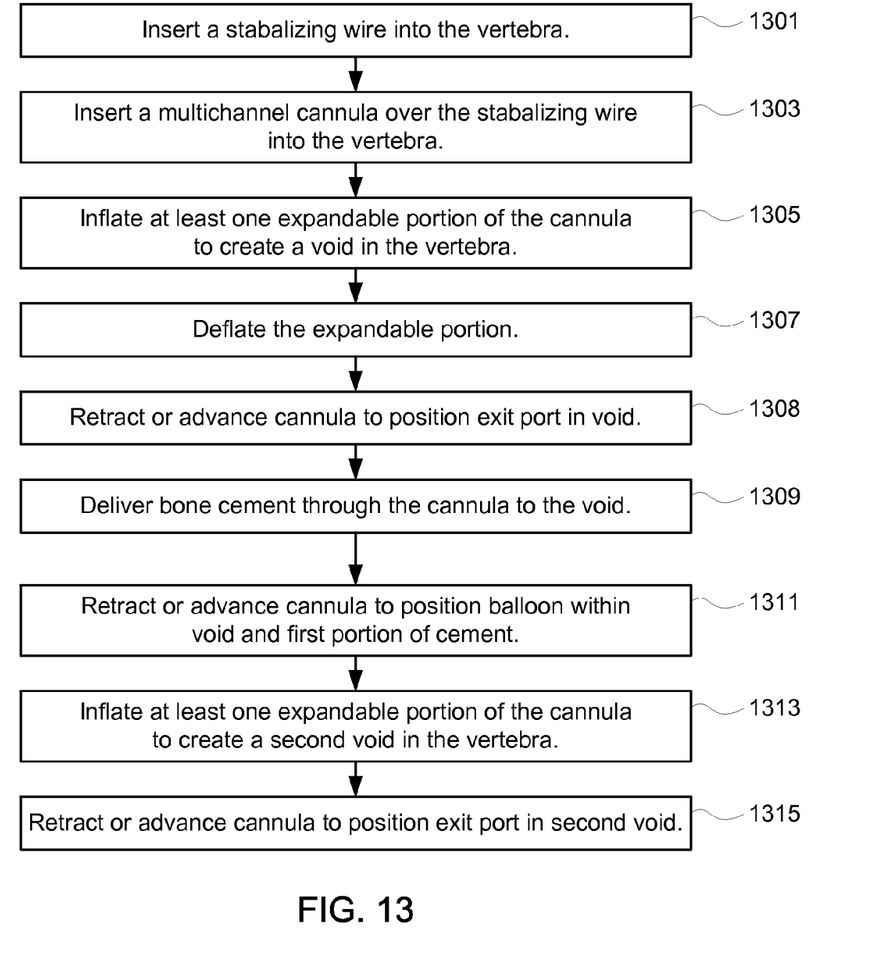
FIG. 13 is a flow chart illustrating the steps of the kyphoplasty method according to FIGS. 9-12.

FIGS. 9-12 depict use of an alternative cannula 210 for performing kyphoplasty of a vertebra, and a method of using cannula 210 is described in FIG. 13. In the exemplary embodiment of FIG. 9, a cannula having a single expandable portion 40 proximal the side exit ports 24 is positioned in the bone, and the expandable portion 40 is inflated to create the void 110. In FIG. 10, expandable portion is deflated and the cannula is retracted slightly to position the side exit ports 24 in the void 110. In this position, bone cement is provided to void 110. Alternatively, the expandable portion 40 for creating the void may be distal to the exit portal, such that the cannula 10 is advanced to position the exit port within the void 110.

As further shown in FIG. 10, the inflatable portion 40 can be re-inflated, to a lesser extent, within aperture 106 to create a plug or stop so that cement does not seep out of the void 110 and into aperture 106 or to other portions of the bone where it is not needed. Though this is shown by using cannula 210, it is contemplated that one or both of expandable portions 40 of cannula 10 could also be used as a plug for this purpose, or an additional expandable portion 40 may be provided on cannula 10 to serve as a plug in aperture 106. To achieve this, expandable portions 40 may be configured to be selectively and separately inflated and deflated such that the expandable portions 40 may be used for different purposes and/or at different times.

FIG. 11 shows an additional optional step in the kyphoplasty method described above, using cannula 210. Once a portion of the cement has been delivered to void 110, the expandable portion 40 may be re-positioned within the void 110 and re-inflated, such that the cement takes on a formation having a second void 112 therein. In this way, the original portion of bone cement creates a shell. Then, following the same manipulation as above in FIG. 10, the cannula 210 may be retracted and second void 112 filled with a second portion of bone cement or another material, such as a bone void filler, as shown in FIG. 12. Using a combination of materials to fill voids 110 and 112 may provide greater longevity in the treatment, and the use of a bone void filler may accommodate bony ingrowth to better support the restored vertebra. This alternative process is not limited for use with a cannula configured as cannula 210, and may be used with cannula 10 or a multichannel cannula having a different configuration.

Not only do the disclosed cannulas provide for a more streamlined and efficient kyphoplasty procedure, but the iterative process as described in FIGS. 11 and 12 would be highly impaired, if not impossible, if multiple introductions and removals of the various devices were required.

The construction and arrangement of the devices and methods as shown in the various exemplary embodiments are illustrative only. Although only a few embodiments have been described in detail in this disclosure, many modifications are possible (e.g., variations in sizes, dimensions, structures, shapes and proportions of the various elements, use of materials, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

What is claimed is:

1. A method of using a multichannel cannula to perform kyphoplasty, comprising:
    inserting a stabilizing wire into a vertebra that is damaged by a compression fracture;
    inserting, over the stabilizing wire, a multichannel cannula into the vertebra, wherein the multichannel cannula comprises:
        a first channel having an open proximal end and an open distal end, wherein the first channel is configured to receive the stabilizing wire;
        a second channel having an inlet portal and an exit portal, wherein the inlet portal and the exit portal are in fluid communication; and
        an outer wall having an expandable portion, wherein the expandable portion is a flexible portion of the outer wall configured to expand away from the multichannel cannula;
    inflating the expandable portion to create a void in the bone and to restore the height of the vertebra that was compromised by the compression fracture;
    deflating the expandable portion; and
    delivering bone cement through the second channel into the void via the exit portal to at least partially fill the void and retain the restored height of the vertebra.

2. The method of claim 1, further comprising re-inflating the expandable portion to modify the void in the bone.

3. The method of claim 2, wherein the position of the expandable portion is adjusted to create a new portion of the void in a different location.

4. The method of claim 2, wherein the expandable portion is inflated at an increased capacity to create a larger void in the bone.

5. The method of claim 1, wherein the expandable portion remains inflated during delivery of the bone cement to create a plug and prevent bone cement from seeping out of the void.

6. The method of claim 1, further comprising advancing or retracting the multichannel cannula after deflating the expandable portion to position the exit portal within the void.

7. The method of claim 1, further comprising re-inflating the expandable portion after delivery of the bone cement such that a second void is formed, the second void at least partially surrounded by bone cement.

8. The method of claim 7, wherein the second void is filled with a second portion of bone cement.

9. The method of claim 7, wherein the second void is filled with a bone void filler.

10. The method of claim 1, wherein the multichannel cannula comprises a plurality of expandable portions.

11. The method of claim 10, wherein the plurality of expandable portions are selectively and independently inflated and deflated during the kyphoplasty procedure.

12. The method of claim 1, wherein the exit portal is a side exit port on the outer wall of the second channel and wherein bone cement is delivered through the second channel to the void via the side exit port.

13. A method of using a multichannel cannula to deliver a material to a void in a bone, comprising:
    inserting a stabilizing wire into a bone;
    inserting, over the stabilizing wire, a multichannel cannula into the bone, wherein the multichannel cannula comprises:
        a first channel having an open proximal end and an open distal end, wherein the first channel is configured to receive the stabilizing wire;
        a second channel having an inlet portal and an exit portal, wherein the inlet portal and the exit portal are in fluid communication; and
        an outer wall having an expandable portion, wherein the expandable portion is a flexible portion of the outer wall configured to expand away from the multichannel cannula;
    inflating the expandable portion to create a void in the bone;
    deflating the expandable portion;
    delivering a material through the second channel into the void via the exit portal to at least partially fill the void.

* * * * *